United States Patent [19]

Vincent et al.

[11] Patent Number: 4,459,089
[45] Date of Patent: Jul. 10, 1984

[54] DIAPHRAGM PUMP WITH IMPROVED PRESSURE REGULATION AND DAMPING

[75] Inventors: Kent Vincent, Cupertino, Calif.; Hans-Georg Haertl, Waldbronn, Fed. Rep. of Germany

[73] Assignee: Hewlett-Packard Company, Palo Alto, Calif.

[21] Appl. No.: 456,195

[22] Filed: Jan. 7, 1983

[51] Int. Cl.³ .......................... F04B 9/08; F04B 11/00
[52] U.S. Cl. .................................. 417/383; 417/540
[58] Field of Search ................ 417/383, 395, 540, 543

[56] References Cited

U.S. PATENT DOCUMENTS 3,984,315 10/1976 Ernst ..................................... 210/349
4,222,414 9/1980 Achener ................................. 138/30

Primary Examiner—Leonard E. Smith
Assistant Examiner—Jane E. Obee
Attorney, Agent, or Firm—Jeffery B. Fromm

[57] ABSTRACT

A new mechanism for pulsation damping in a reciprocating diaphragm pump system is disclosed which is especially suitable for solvent delivery in modern high pressure liquid chromatography requiring a wide range of solvent flow rates and pressures. The disclosed damper has good overall performance over the full range of liquid chromatographic conditions, a dead volume independent of solvent pressure, and largely eliminates the necessity for continuously pumping the working oil of the diaphragm pump to a maximum operating pressure.

11 Claims, 7 Drawing Figures

DIAPHRAGM PUMP WITH IMPROVED PRESSURE REGULATION AND DAMPING

BACKGROUND OF THE INVENTION

Diaphragm pumps have found wide application because of the fact that they work essentially leak free, as compared to conventional piston pumps, and do not contain parts as susceptible to wear, which may also contribute to contaminating the pumping medium. In diaphragm pumps, the diaphragm is not directly driven by a mechanical component, but rather is driven through a hydraulic pressure medium, usually oil, and hereinafter referred to as oil, which in turn is activated by a mechanical piston. This piston is not particularly susceptible to sealing problems since leakage oil, if any, may be supplied to an oil reservoir from which the oil volume between the piston and the diaphragm is automatically refilled. In this type of pump, the diaphragm forms the boundary between the pumping medium to be delivered and the working oil.

High pressure liquid chromatography (HPLC) is one of the fields of application of diaphragm pumps of the type described above. Growth in this technology has been toward increasing pressures at ever decreasing flow rates. Here, a disadvantage inherent in the design of diaphragm pumps makes itself felt, namely the pulsating flow of the liquid delivered. When a diaphragm pump is used in liquid chromatography, it is necessary that this pulsation be damped enough to ensure that it will not vitiate the analysis. To effect this damping, one generally employs damping elements containing the medium delivered which are adapted to increase their volume as the pressure rises and to reduce it again when the pressure drops. Thus, a "capacitor effect" is achieved meaning that part of the medium delivered by the pump is stored during the pressure phase and released again via a flow resistance during the other phase of the pump when its pressure drops at the high pressure end. In this manner, a certain uniformity of flow is achieved.

A damper of this type is described by Achener, U.S. Pat. No. 4,222,414, issued Sept. 16, 1980 wherein delivered fluid is caused to pass through a sealed expandable plastic tube immersed in a sealed chamber of a compressible liquid. A pressure pulse in the delivered fluid is damped by the radial expansion of the plastic tube into the compressible liquid. Bourdon tubes and compressible liquid or spring loaded diaphragms also are typical of the above described damping technique. The function of these prior art dampers is similar to that of RC elements in an electrical circuit; namely the damping behavior is a function of the pumping frequency. In addition, the equilibrium volume of the damping element increases as the absolute pressure of the delivered medium rises creating dead volume which is undesirable in modern high pressure liquid chromatography. For example, in light of the present tendency to ever smaller flow quantities and ever higher pressures, a dead volume of even 1 ml is unacceptable, since it would appreciably widen the peak in an HPLC chromatogram.

Ernst, et al., U.S. Pat. No. 3,984,315 issued Oct. 5, 1976 describes a damping device which predominatly overcomes the limited performance range of prior art RC type dampers. Here, a manually adjustable spring is coupled to the diaphragm of a diaphragm damper to provide adjustable stiffness to the damping chamber. When used at high absolute fluid pressures the spring is manually compressed to raise the effective stiffness of the diaphragm and restrict the dead volume expansion of the damper chamber. At low fluid pressures the stiffness is adjusted accordingly lower. In this manner, an appropriate balance between damping and dead volume can be adjusted for a given pump operating pressure condition. The primary shortcoming of this technique is the inconvenience of the manual set point adjustment and the fact that in liquid chromatography operating pressures are not always constant; a loss in absolute pressure would cause diminished damping, whilst a gain in absolute pressure would cause a rise in dead volume for a given spring preload.

A second disadvantage of diaphragm pumps concerns the need to provide a means for regulating the oil pressure developed between the piston and diaphragm. Once the diaphragm has reached its full deflection with hydraulic pressure, any residual stroke of the diaphragm pump piston will incur a rapid pressure increase of the oil over the diaphragm pressure which could be damaging to the diaphragm, pump seals and valves. In the prior art measures to limit excessive oil pressure development have consisted of the placement of a pressure regulating valve in the oil chamber between the piston and diaphragm to vent the high pressure oil back to the pump oil reservoir, or the placement of a preloaded spring between the piston and its drive mechanism to restrict piston displacmeent beyond an oil pressure set point. In either case, the oil override set point must be set at an oil pressure greater than the maximum downstream delivered fluid pressure to insure sufficient oil pressure to cause proper deflection of the diaphragm with each stroke of the piston over all operating conditions and delivery pressures. Since in liquid chromatography the analysis is most often obtained at average pump pressures substantially below the maximum operating point of the pump, the prior art diaphragm pump is usually substantially overworked, causing premature wear of seals, valves, and other parts in each pump.

SUMMARY OF THE INVENTION

In accordance with the illustrated preferred embodiment the present invention provides a damping system which achieves efficient damping of the pulsations of a diaphragm pump of the delivered medium over a range from high to extremely low delivery volumes over a broad range of low to high pressures, without giving rise to any significant dead volume. Simultaneously, with the delivery of the medium to be delivered, the diaphragm pump of the invention delivers a flow of the pressure medium, e.g., oil, into a damper vessel. The pressure in the damper vessel builds up with a certain delay relative to the pressure in the damper chamber because the flow resistance that must be overcome by the pressure agent is somewhat higher than that which must be overcome by the liquid to be delivered. The damper vessel is equipped with a pressure medium outlet which communicates with atmospheric pressure via a valve with variable flow resistance. When the pressure in the damper vessel is lower than the pressure in the damper chamber, this flow resistance is increased so that the pressure in the damper vessel rises until an equilibrium is reached between the mean pressure in the damper chamber and the pressure in the damper vessel. When the pressure in the damper vessel is higher than the pressure in the damper chamber, the flow resistance of the valve decreases so that again a pressure equilibrium is reached between the damper chamber and the damper vessel. Because of the delay with which the pressure is balanced between the pressure medium reservoir of the pump and the damper vessel, the pressure pulsations occurring in the pressure medium reservoir are not transmitted to the damper vessel. In contrast, the pressure encountered in the damper vessel is always equal to the mean value of the pulsating pressure in the damper chamber, irrespective of the absolute pressure level. This means that the resilient partition wall between the damper chamber and the damper vessel moves invariably about a constant mean position so that the mean volume of the damper chamber remains constant, irrespective of the absolute pressure existing at any time. Accordingly, the dead volume does not change as the absolute pressure changes.

According to the invention, the volume of the damper chamber of the pump of the invention may have a size small enough (on the order of 0.1 ml) to make it suited also for use in modern highpressure liquid chromatography with minimum flow quantities. Thus, since the volume of the damper chamber can be made small and the average volume can be kept constant as the absolute pressure is varied, the present invention is well suited for use over a broad range of operating pressures. In addition, since the damper chamber serves as a constant averaging load for the pump, the pumping chamber of the pump need only be pressurized to a pressure just exceeding the desired output pressure for the medium to be delivered. The result is that the pump itself is subjected to less wear and tear than pumps in the prior art which must operate continuously at the maximum operational pump pressure.

In particular, the resilient partition wall (diaphragm) between the damper chamber and the damper vessel may be an integral part of the valve with variable flow resistance. To this end, the output opening of the damper vessel is arranged near the partition wall in a manner such that it will be covered up by the latter to a greater or lesser extent, depending on the differential pressure between the damper chamber and the damper vessel.

The invention will now be described with reference to certain embodiments and to the pertinent drawings.

DETAILED DESCRIPTION OF THE PREFERRED EMBODIMENT

Figure 1:
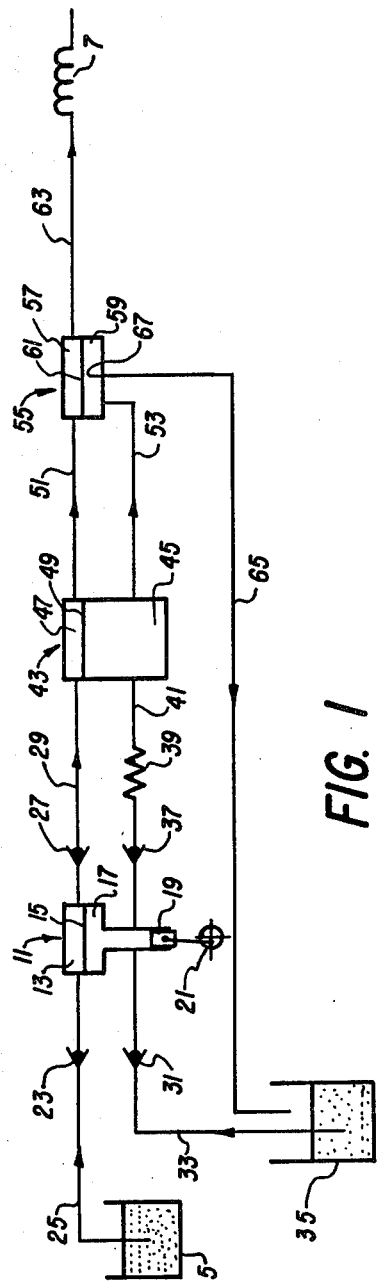
FIG. 1 shows a basic diagram of a diaphragm pump and damper system of the invention.

In FIG. 1, reference number 11 designates the pumping section of a diaphragm pump. The pumping section 11 includes a pumping chamber 13 for a liquid to be delivered, such as a solvent in an LC system, from a solvent reservoir 5 to a load 7 such as an LC column. The pumping chamber 13 is separated by a diaphragm 15 from a pressure medium chamber 17 filled with a hydraulic pressure medium such as oil, or other suitable medium. A piston 19 is actuated by a crank mechanism 21 to perform a reciprocating movement in the oil chamber 17.

The pumping chamber 13 is connected via an input valve 23 and a suction line 25 to solvent reservoir 5 for the fluid to be delivered, and via an output valve 27 to a high-pressure line 29. The oil chamber 17 communicates with an oil reservoir 35 via an input valve 31 and a suction line 33, and with an oil line 41 via an output valve 37; a resistance element 39 provides a specific flow resistance. The design of the output valve 37 is such that it will open only at a pressure substantially higher than that causing the output valve 27 to open.

A damper arrangement 43 includes a damper vessel 45 and a damper chamber 47 separated from each other by a flexible diaphragm 49. The damper chamber 47 communicates with the solvent high pressure line 29, while the damper vessel 45 communicates with the oil pressure medium line 41. Connection lines 51 and 53 connect the damper chamber 47 and the damper vessel 45, respectively, with a differential-pressure controlled valve 55.

The differential pressure controlled valve 55 has two pressure chambers 57 and 59 separated from each other by a flexible diaphragm 61. The pressure chamber 57 communicates with the solvent connection line 51, while the pressure chamber 59 communicates with the oil connection line 53. Also connected to the pressure chamber 57 is an output line 63 for the liquid to be delivered to load 7. An oil vent 65 leads from the pressure chamber 59 back to the oil reservoir 35.

The oil vent 65 terminates in an opening 67 located in the pressure chamber 59 near the diaphragm 61. When the solvent pressure in the chamber 57 exceeds the oil pressure in the chamber 59, the diaphragm 61 is deformed towards the opening 67. Conversely, the diaphragm 61 is deformed away from the opening 67 when the oil pressure in the chamber 59 exceeds the solvent pressure in chamber 57. The diaphragm 61 and the opening 67 coact to ensure that the flow resistance for the oil flowing through the pressure medium vent 65 increases continuously as the diaphragm 61 approaches the opening 67.

The function of the arrangement described above is as follows:

The reciprocating movement of the piston 19 causes the oil in the pressure medium chamber 17, and consequently, the diaphragm 15 to move to and fro. As a result, the input valve 23 and the output valve 27 open and close respectively so that solvent is delivered from the suction line 25 to the highpressure line 29. It is an inherent feature of the design that the solvent delivery takes place in a pulsating manner. To eliminate or greatly reduce pulsations the solvent is initially supplied into the damper chamber 47 of the damper arrangement 43. Together with the input valve 31 and the output valve 37, the oil chamber 17 coacts with the piston 19 to operate as a normal piston pump by means of which oil is delivered from the pressure medium reservoir 35 to the damper vessel 45 of the damper arrangement 43. However, because the output valve 37 requires a higher pressure to respond than the output valve 27, this latter operation will start only upon completion of the delivery phase of the solvent. And given the fact that the oil flow must pass the flow resistance 39, it must overcome a much higher flow resistance than the liquid in the high pressure line 29. Accordingly, the pressure in the damper vessel 45 follows the pressure in the damper chamber 47 with a certain delay.

The volume of the damper vessel 45 is large enough so that under operating pressure conditions (in high pressure liquid chromatography up to 500 bars) the compressibility of the oil in the damper vessel 45 is high enough to permit the volume of the damper chamber 47 to vary sufficiently to obtain the desired damping of pulsations in the high pressure line 29. For example, damper vessel 45 may have a volume of 15–35 ml, containing oil of compressibility $65 \times 10^{-6}$ bar$^{-1}$.

The pressure in the oil damper vessel 45 adapts itself continuously to the mean pressure in the solvent damper chamber 47. This results from deformation of diaphragm 61 toward the opening 67 when the pressure in the solvent pressure chamber 57 exceeds the pressure existing in the oil pressure chamber 59. Flow of oil out of opening 67 is reduced, thereby causing the pressure in the oil pressure chamber 59 to rise until an equilibrium is achieved. Similarly, when the pressure in the oil pressure chamber 59 exceeds the pressure in the solvent pressure chamber 57 oil flow from opening 67 is increased, reducing the pressure in chamber 59. The flow resistance 39 and the flow resistance in the opening 67 cause the pressure in the damper vessel 45 to change only slowly, as compared to the pressure in the damper chamber 47. Thus, a quasi-static counter pressure is obtained for the damper chamber 47. Since this counter pressure is always equal to the mean pressure in the damper chamber 47, the diaphragm 49 moves constantly about its neutral central position, irrespective of the absolute pressure existing at any time in the system. If, however, the damper vessel 45 were closed, the increasing mean pressure in the damper chamber 47 would cause the diaphragm 49 to bulge further and further into the damper vessel 45, and as a result thereof the dead volume of the damper chamber 47 would increase with rising pressure. This situation is prevented by the arrangement described above.

Figure 2:
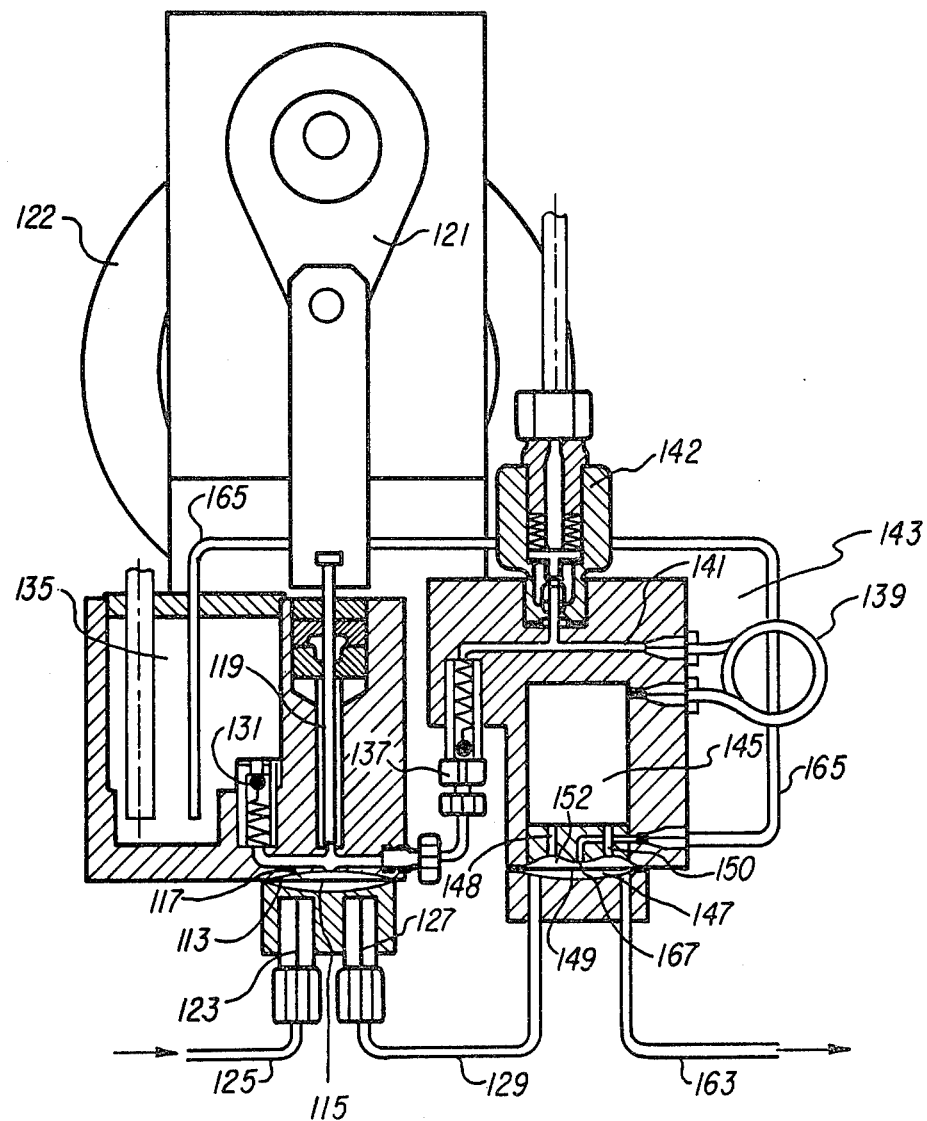
FIG. 2 is a diagrammatic representation of a practical embodiment of the diaphragm pump and damper system of the type shown in FIG. 1.

FIG. 2 is a diagrammatic representation of a practical embodiment of the diaphragm pump shown in FIG. 1. A pumping chamber 113 is separated by a diaphragm 115 from a pressure medium (oil) chamber 117 in which a piston 119 reciprocates. The piston 119 is driven by a motor 122 via a crank mechanism 121.

The pumping chamber 113 communicates via an input valve 123 with a suction line 125 and via an output valve 127 with a highpressure line 129. The oil chamber 117 communicates via an input valve 131 with an oil reservoir 135. An output valve 137 and a flow resistance loop 139 connect the oil chamber 117 to a damper vessel 145 provided in a damper arrangement 143. Between the output valve 137 and the flow resistance loop 139 there is connected to the connection line 141 a pressure relief valve 142 which serves to prevent damage to the individual elements of the diaphragm pump in the event the flow of pumped liquid should be blocked for any reason whatever.

The damper arrangement 143 includes a damper vessel 145 with a diaphragm 149. The damper chamber 147 communicates, on the one hand, with the solvent high pressure line 129 and, on the other hand, with a solvent output line 163. The damper vessel 145 communicates with a valve chamber 152 via channels 148 and 150. The diaphragm 149 is firmly held about its periphery between the damper chamber 147 and the valve chamber 152. The shape of the damper chamber 147 and the valve chamber 152 is preferably such that the diaphragm 149 may abut against the wall on either side without damage.

A pressure medium vent 165 opens into the valve chamber 152 through an opening 167 which is closed to a greater or lesser extent in response to the pressure difference between the damper chamber 147 and the damper vessel 145 or the valve chamber 152, respectively, the function being substantially the same as that of valve 55 in FIG. 1.

The diaphragm pump arrangement shown in FIG. 2 may be constructed of such a small size that the dead volume of the liquid delivered may be kept as low as 50 ul, while a hydrostatic pressure of 450 bars can be achieved. The damping arrangement permits the restriction of the pressure variations in output line 163 to 10 bars. A conventional passive damping arrangement would have a dead volume of 1 ml at 450 bars.

Figure 3:
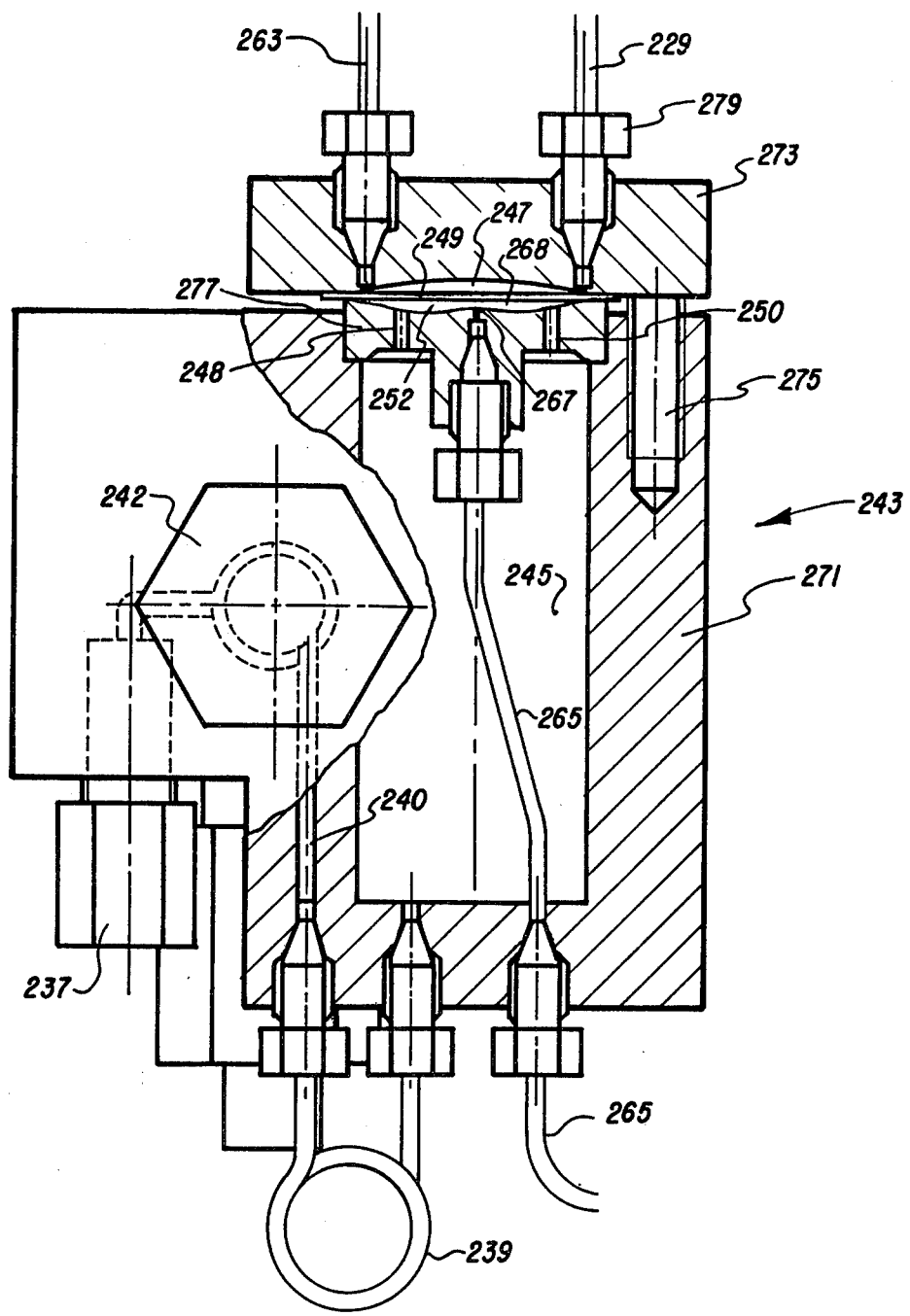
FIG. 3 is a part-sectioned longitudinal view of the damper chamber and the damper vessel.

FIG. 3 shows the detail of a damper arrangement 243 of a design similar to that of damping arrangement 143 in FIG. 2. A damper vessel 245 communicates with a valve chamber 252 via channels 248 and 250. The valve chamber 252 is separated by a diaphragm 249 from a damper chamber 247 into which open a high pressure line 229 arriving from the pumping chamber and an output line 263.

The damper vessel 245 communicates via a flow resistance loop 239 and a connection line 240 with an output valve 237 from the oil chamber of the pumping arrangement (not shown in FIG. 3). As in the arrangement shown in FIG. 2, a pressure relief valve 242 is connected to the connection line 240. An oil vent 265 opens through an opening 267 into the valve chamber 252. The opening 267 is provided in a protrusion 268, whose detailed shape will be described in more detail below.

The damper arrangement 243 includes two housing portions 271 and 273 clamped together by screws 275, of which only one is shown in FIG. 3. Between the housing portions 271 and 273, an insert 277 includes two channels 248 and 250 and the opening 267. The individual components may be constructed of a pressure and corrosion resistant material suited for the liquid to be delivered. For example, the lines shown in FIG. 3 may be capillary tubes of corrosion resistant steel and connected in sealing relationship to the respective portions of the damper arrangement 243 by means of commercial attachment fittings 279.

As in the arrangement shown in FIG. 2, the surfaces of the housing portion 273 and the insert 277 facing the diaphraph 249 are only slightly rounded so that the diaphragm 249 may abut against them without being damaged. In order to ensure that the diaphragm 249 will not adhere to said surfaces, the surfaces are finished with sufficient roughness to prevent suction between the diaphragm 249 and the surfaces. Grooves may also be applied to said surfaces to achieve the same purpose.

Figure 4:
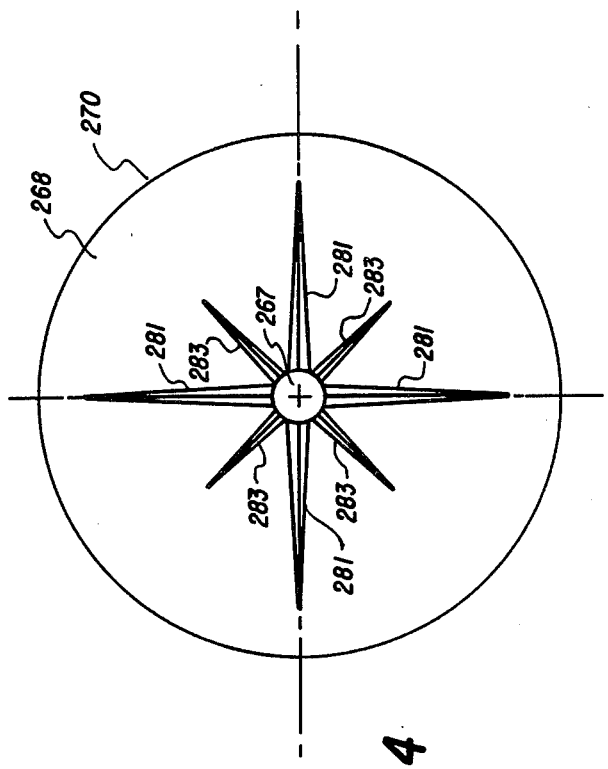
FIG. 4 shows the details of the output opening of the damper vessel in the arrangement shown in FIG. 3.

FIG. 4 shows a preferred embodiment of the opening 267 and its surroundings in a somewhat enlarged scale. The circular line 270 defines the outline of the spherical protrusion 268 at the center of which the opening 267 can be seen. On the spherical protrusion 268 grooves 281 and 283 are provided emerging radially from the opening 267, the grooves 283 being somewhat shorter than the grooves 281. For example, grooves 283 may be 2 mm in length, while grooves 281 are 3 mm long. The grooves 281 and 283 are triangular in cross-section and become flatter with increasing distance from the opening 267. Now, when the diaphragm 249 is in full contact with the spherical protrusion 268, the opening 267 is fully closed. When the diaphragm 249 begins to lift off the spherical protrusion 268, the ends of the grooves 281 will be released first so that a small flow of pressure medium will be permitted to flow from the damper vessel 245 into the opening 267. As the diaphragm continues to lift off of spherical protrusion 268, the cross-section through which the pressure medium can flow off increases, especially since the grooves 283 also become active. Finally, when the diaphragm 249 has fully come off the spherical protrusion, the flow resistance is solely determined by the distance between the diaphragm 249 and the opening 267.

The grooves 281 and 283 guarantee a smooth flow resistance characteristic for the pressure medium flow, in response to the position of the diaphragm. Grooves 281 and 283 also provide a means to match the oil flow rate from the pump to the specific flow resistance needed to obtain damper stability. Thus the grooves 281 and 283 would be enlarged for higher oil flow rates or visa versa.

The embodiments described herein do not limit the teachings of this invention. For example, it would be obvious to one skilled in the art that the pressure control valve 55 of FIG. 1 could consist of a differential pressure transducer and a motor or electrically operated valve. The differential pressure transducer would electrically sense average pressure changes between the solvent and oil in pulse damper 43 and provide thereby feedback for electronically controlling the flow resistance of oil through the electrically operated valve and the oil pressure in damper chamber 47. Such a system could include electrical filtering to limit transient response and hence further stabilize damper operation. It would also be obvious to one skilled in the art that the diaphragm 49 and damper chamber 47 could consist of a sealed expandable plastic tube immersed in the damper vessel 45.

We claim:

1. An apparatus for damping pulsations in a liquid to be delivered in a liquid delivery system, said apparatus comprising:
    a pump having a pumping chamber through which the liquid to be delivered flows and a pressure medium chamber pressurized with an hydraulic medium, the pumping chamber and the pressure medium chamber separated by a first diaphragm;
    a pulse damper having a damping chamber and a damper vessel separated by a resilient wall, wherein the damping chamber is coupled to the pumping chamber and the damper vessel is coupled to the pressure medium chamber; and
    a differential pressure means coupled across the resilient wall for measuring the average pressure difference between the damper chamber and the damper vessel and maintaining the average pressure difference substantially constant independent of the absolute pressure in the damper chamber.

2. An apparatus for damping pulsations in a liquid to be delivered in a liquid delivery system, the apparatus comprising:
    a pump having a first diaphragm activated by an hydraulic pressure medium which is moved by a piston within a pressure medium chamber, the first diaphragm being a boundary of a pumping chamber for the liquid to be delivered, said pumping chamber having a first input valve and a first output valve, and said pressure medium chamber connected to a pressure medium reservoir via a second input valve;
    a pulse damper having a damper vessel separated by a resilient wall from a damper chamber through which the delivered liquid flows, the damper vessel having a volume of a size that allows a perceptible compression of the pressure medium contained therein and connected to the pressure medium chamber via a second output valve, the second output valve having a flow resistance greater than the flow resistance of the first output valve; and
    a pressure medium vent connected to the damper vessel via a pressure valve with variable flow resistance controlled by the average pressure difference between the damper vessel and the damper chamber so that at higher pressure in the damper chamber the flow resistance of the pressure valve is increased, and visa versa.

3. An apparatus as in claims 1 or 2 wherein the damping chamber and the resilient wall comprise a resilient tube submerged in the damping vessel.

4. An apparatus as in claim 2 wherein the second output valve is arranged to open at higher pressure than the first output valve.

5. An apparatus as in claims 1, 2 or 4 further comprising a resistance element for increasing the flow resistance arranged between the second output valve and the damper vessel.

6. An apparatus as in claim 2 wherein the resilient wall between the damper chamber and the damper vessel is arranged to control the pressure valve with variable flow resistance.

7. An apparatus as in claim 6 wherein the pressure valve with variable flow resistance further comprises an opening adjacent to the resilient wall, which opening is connected to the pressure medium vent.

8. An apparatus as in claims 1 or 7 wherein the resilient wall is a second diaphragm.

9. An apparatus as in claim 8 wherein the wall of the damper chamber facing the second diaphragm and an abutment arranged within the damper vessel and facing the other side of the second diaphragm are shaped in such a manner that the second diaphragm may abut them without being harmfully deformed.

10. An apparatus in claim 9 wherein the opening further comprises a plurality of grooves.

11. An apparatus as in claim 9 wherein the opening is located in a substantially spherical protrusion of the abutment, the protrusion facing the diaphragm, and further comprising:
    a plurality of grooves on the protrusion emerge radially from the opening and become flatter with increasing distance from the opening.